United States Patent [19]

Guirguis et al.

[11] Patent Number: 4,912,057
[45] Date of Patent: Mar. 27, 1990

[54] CELL CHAMBER FOR CHEMOTAXIS ASSAY

[75] Inventors: Raouf A. Guirguis, Rockville; Richard H. Goodwin, Cabin John, both of Md.

[73] Assignee: Cancer Diagnostics, Inc., Rockville, Md.

[21] Appl. No.: 365,417

[22] Filed: Jun. 13, 1989

[51] Int. Cl.[4] .............................................. C12M 3/04
[52] U.S. Cl. .................................. 435/285; 435/300; 435/301
[58] Field of Search ............... 435/285, 284, 286, 297, 435/298, 300, 301, 299, 240

[56] References Cited

U.S. PATENT DOCUMENTS

| | | | |
|---|---|---|---|
| 3,821,087 | 6/1974 | Knazek et al. | 435/285 |
| 4,087,327 | 5/1978 | Feder et al. | 435/285 |
| 4,201,845 | 5/1980 | Feder et al. | 435/285 |
| 4,228,243 | 10/1980 | Iizuka | 435/285 |
| 4,299,920 | 11/1981 | Peters | 435/285 |
| 4,304,865 | 12/1981 | O'Brien et al. | 435/285 |
| 4,324,859 | 4/1982 | Saxholm | 435/33 |
| 4,326,028 | 4/1982 | Brown | 435/32 |
| 4,634,676 | 1/1987 | Supatino | 435/294 |
| 4,661,458 | 4/1987 | Berry et al. | 435/284 |
| 4,720,462 | 1/1988 | Rosenson | 435/285 |
| 4,748,124 | 5/1988 | Vogler | 435/240 |

OTHER PUBLICATIONS

Author: Neuro Probe Inc., Title: Blind Well and Boyden Chambers, Date: Copyrighted 1988, Pertinent Pages: Entire pamphlet.
Author: Neuro Probe Inc., Title: 48 Well Micro Chemotaxis Chamber, Date: Copyrighted 1988, Pertinent Pages: Entire pamphlet.
Author: Neuro Probe Inc., Title: 10 Well Chemotaxis Chamber, Date: copyrighted 1988, Pertinent Pages: Entire pamphlet.
Author: Neuro Probe Inc., Title: 12 Well Manifold Chamber, Date: Copyrighted 1988, Pertinent Pages: Entire pamphlet.
Author: Neuro Probe Inc., Title: Single Well and four Well Separation Chambers, Copyrighted 1988, Pertinent Pages: Entire pamphlet.
Author: Neuro Probe Inc., Title: Zigmond Chamber Date: Copyrighted 1988, Pertinent Pages: Entire pamphlet.
Author: Neuro Probe Inc., Title: Three-Tiered Chamber, Date: Copyrighted 1988, Pertinent Pages: Entire pamphlet.

*Primary Examiner*—James C. Yeung
*Attorney, Agent, or Firm*—John S. Hale

[57] ABSTRACT

A chemotaxis assay instrument comprising a plate assembly with a bottom plate, a gasket seal mounted to the bottom plate and an intermediate plate mounted on the other side of the gasket seal and spaced by the gasket seal from the bottom plate. The intermediate plate defines a plurality of wells to hold a sample and a filter membrane is mounted on the intermediate plate. A second intermediate plate is spaced from the first intermediate plate by the filter membrane and second gasket seal is mounted on the other side of the second intermediate plate with a top plate mounted on said second gasket seal and spaced by the second gasket seal from the second intermediate plate, the plate assembly being held together by fasteners in a sealed relationship.

22 Claims, 2 Drawing Sheets

PRIOR ART   FIG. 2A

CELL CHAMBER FOR CHEMOTAXIS ASSAY

BACKGROUND OF THE INVENTION

Mammalian cells are usually cultured in glass or plastic vessels, either in suspension or as an attached layer, completely surrounded by culture media. Pseudopodia protrusion is a prominent feature of mammalian cells both invitro and invivo. Through their surfaces, cells can interact and sense the changes in the outside world. In studies of model membrane systems, steps in the fusion of membrane have been identified. In order for the fusion process to take place, certain requirements have to be fulfilled. Initially the membranes have to be close enough to make contact. This is generally prevented by large membrane glycoproteins which sterilly hinder the membranes preventing a close enough contact to allow fusion. Because of the charged surface of the membranes, they may repel, thereby preventing any closer contact. Therefore, there must be some mechanism within the cell to control which membrane will undergo fusion. This may be regulated by specific fusion proteins similar to the ones isolated from the influenzia and sendia virus.

The use of chambers for cell culture and chemotaxis assay is known in the prior art.

U.S. Pat. No. 3,821,087 discloses an apparatus having semi-permeable tube shaped membranes allowing the growth of cells invitro. Cells are allowed to settle on the outside surfaces of the membranes in a nutrient medium environment while the membranes are continuously profused with oxygenated nutrient medium flowing through the membranes. The nutrient substances diffuse from the perfusing medium through the membrane wall and into the cells, while cell products diffuse from the cell through the membrane wall into the perfusate from which the cell's products may be recovered.

U.S. Pat. Nos. 4,087,327 and 4,201,845 are directed to a cell culture reactor used in the growth of cells invitro which employs elongate selectively permeable hollow fibers arranged in a shallow layer configuration as a matrix for cell attachment on the outer surface of the fibers. The flow path of the culture medium is directed by a distributor plate which serves as a manifold to provide uniform distribution of the medium through the fibers and a flow path which is upward and transverse to the plane of the elongate axis of the fibers.

U.S. Pat. No. 4,228,243 discloses an apparatus and method for propagating tissue cultures in a plurality of stacked frames and plates which are clamped together. The plates are stacked on resilient gaskets which are provided to stop leakage between the uppermost dish and coverplates and overflow passages are provided in the plates through which the media, cell suspensions and gases can pass.

U.S. Pat. No. 4,299,920 discloses a receptacle for cell cultures constructed of a base plate with a wall assembly defining a plurality of chambers detachably, adhesively joined to the base plate. The portion of the wall assembly adjacent to the base plate consists of a non-cytotoxic elastomeric synthetic material which adheres to the base plate in a liquid-tight manner. On completion of cultivation of the cells the base plate can be manually separated from the wall section.

U.S. Pat. No. 4,304,865 discloses an apparatus having a harvester plate with a plurality of wells recessed into one surface. A disc-shaped sheet of filter paper placed over the top surface of the harvester plate and a modified Terasaki plate with an outer wall section and conically shaped wells recessed into its surface is mounted over the filter paper and harvester plate. When the plate is maintained in an upside down orientation the material is transferred directly to the filter paper disc.

U.S. Pat. No. 4,324,859 discloses a microbiological container with a substrate having insertable elements. The lower edge of each element forms a sealed relationship with the bottom of the container forming separate regions with isolated substrate portions. A cover can be placed on the insertable element in order to cover the respective isolated section.

U.S. Pat. No. 4,326,028 discloses a cylindrical dish with two cylindrical compartments divided by a perforated jell support structure with a temporary seal. After the microorganisms are grown in compartment A, the dish is inverted, the seal removed, and a second nutriate medium poured into compartment B.

U.S. Pat. No. 4,634,676 discloses a replica plating device comprising a container which holds cells and a skirted press member which fits into the container. Attached to the exterior bottom surface of the bottom wall of the press member is a layer of compressible material such as soft expanded polyurethane or hard polyurethane foam. The compressible material serves to cushion the pressing effect of the replica plating device against the cells and culture medium during use.

U.S. Pat. No. 4,661,458 discloses a device used for the culture of cells incorporating several modules of different functions for regulating the cell growth environment, providing a suitable cell growth substrate or separating the desired product from interfering substances. Each module is constructed of a series of membranes separated by a solid support material which is channeled to provide a series of parallel capillaries for the flow of fluids.

U.S. Pat. No. 4,720,462 discloses a culture tube divided into five sealed chambers with cell impermeable hydrophilic tubes extending from one chamber to another chamber.

A cell permeable filter tube extends along the initial horizontal axis of the straight culture tube from one end of the culture chamber to the other. The filter tube has an average porosity over 100 microns, preferably between about 100 and 500 microns such that under normal operating conditions of cell sloughage the tube does not occlude. Cells are forced under pressure into the tube and through the wall of the cell permeable tube.

U.S. Pat. No. 4,748,124 discloses a closed cell culture device using spaced sheets of gas permeable, liquid impermeable material with a third sheet sandwiched between the first and second spaced sheets which is selectively permeable to a class of molecules having a molecular weight ranging from 8,000 to 15,000 molecules. All of the sheets are held in a housing chamber formed by four concentric ring members, the first and third sheets define a first closed compartment and the second and third sheets define a second enclosed compartment with each compartment having an access port. The rings are sealed together in compression by attachment screws.

The use of a small diameter pore filter which is small enough to prevent whole cell migration in the chemotaxis assay allows the cells to first extend their pseudopodia to a lower compartment while the cell nuclei remain in the upper compartment. Consequently the separation between the two compartments by mono layered cells anchored to the filter through their extended pseudopodia permits the collection of extended pseudopodia as well as substances secreted into the lower walls. Thus, depending on the pore size of the filters, the pseudopodia chamber can be used for the study of either whole cell migration or cell pseudopodia protrusion. Although cell pseudopodia is not new to researchers studying cell movement, no one has previously been able to isolate these cellular processes. Furthermore, in order to study the morphological changes involved in the intermediate steps between triggering the chemotactic signal and the end result i.e. cell locomotion, one had to rely on a complicated technique such as time lapse cinemotagraphy. The results of such cinemotagraphy are difficult to interpret as well as uncertain.

One prior art assay for enutorphoril chemotaxis which ha been widely used for studying cell movement is the Boyden chamber assay which is shown in FIGS. 1 and 1A. The Boyden chamber is composed of two parts which constitute an upper and a blind lower well. Chemo attractants are added to the lower well before placing the membrane which separates the lower from the upper well. In this assay the conditions in the lower well cannot be changed once the experiment has been started. A second prior art chamber which has been used for chemotaxis assay is shown in FIGS. 2 and 2A. This chamber is composed of a bottom plate with a single or multiple blind wells, a filter and a top plate with matching diameter wells which is attached to the bottom plates by a series of bolts. In contradistinction to this device, the newly designed inventive chamber provides free access to both the upper as well as the lower wells throughout the experiment. This permits the study of isolated or intact pseudopodial protrusions independent from their cell bodies. Moreover, since the cell monolayer can physically separate the two compartments in the new chamber, one can further study the changes in cell responses to different legans after changing the conditions in either the upper or lower wells or both.

SUMMARY OF THE INVENTION

A chemotaxis assay instrument comprising a bottom plate, a gasket filter mounted to said bottom plate surface and, an intermediate plate defining a plurality of wells to hold a sample mounted on the other side of said gasket filter, form one compartment of the instrument. A second intermediate plate is spaced from the first intermediate plate by a polycarbonate membrane filter having a pore size ranging from 3 to 8 microns. A top plate is mounted to the first intermediate plate with a gasket filter positioned between the top plate and second intermediate plate to form a second compartment of the instrument. Bolts hold the plates and filter membrane together in a sealed relationship.

It is an object of the present invention to provide an apparatus for the simple, economical and effective culture of cells.

It is a further object of the present invention to provide for a means of collecting and/or removing cell pseudopodia.

It is yet another object of the present invention to allow free access to upper and lower wells at any time during the assay without disturbing the cell pallet.

These and other objects and advantages of the present inventive apparatus will become more readily apparent in the following detailed description thereof together with the appended drawings.

BRIEF DESCRIPTION OF THE DRAWINGS

FIGS. 2 and 2A are top plan and exploded cross section views of another prior art chemotaxis chamber;

DETAILED DESCRIPTION OF THE INVENTION

Figure 1:
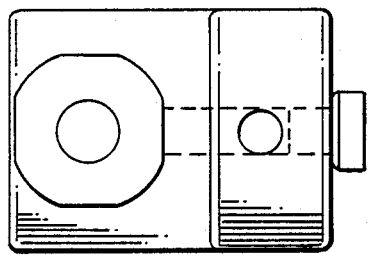
FIGS. 1 and 1A are respectively top plan and exploded cross sectional views of the prior art Boyden chamber.
Figure 1A:
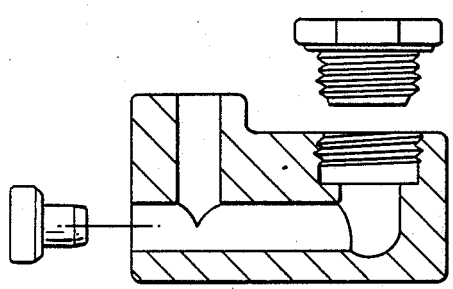
Figure 1A:
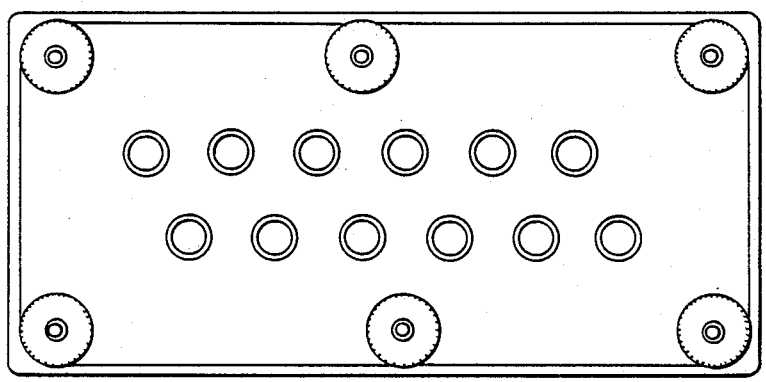
Figure 2:
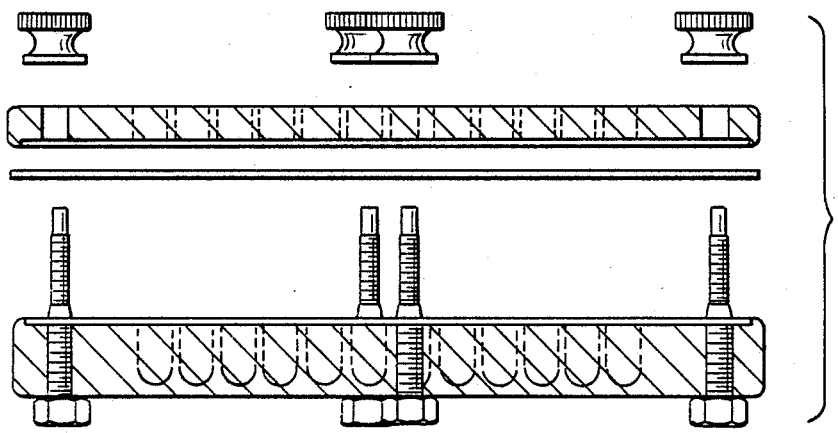
Figure 3:
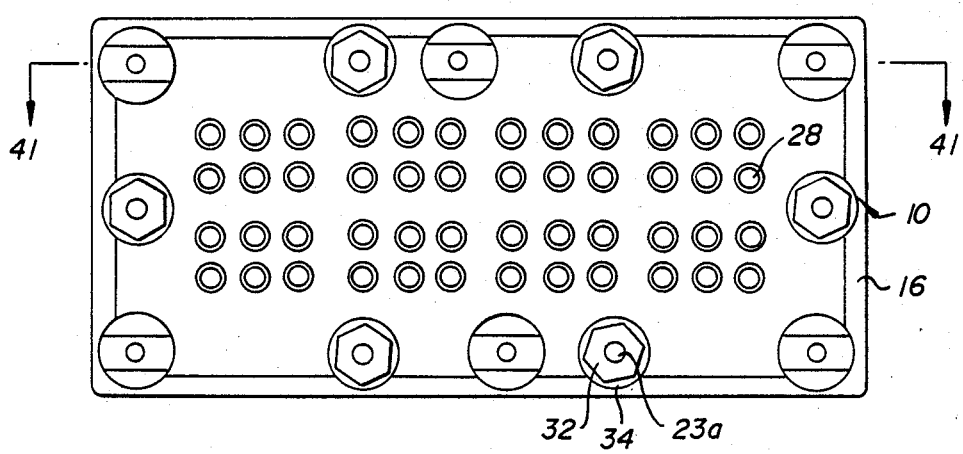
FIG. 3 is a top plan view of a preferred embodiment of the invention.
Figure 4:
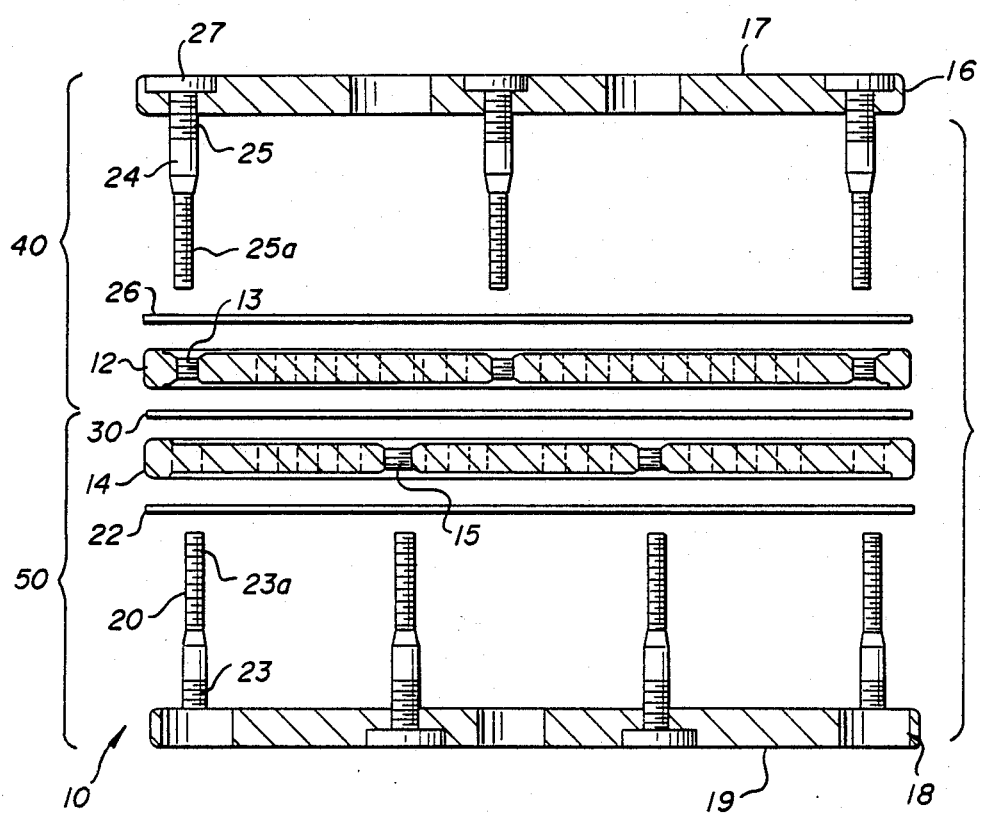
FIG. 4 is an exploded cross sectional view of the preferred inventive chamber embodiment as viewed across line 4'—4' of FIG. 3.

The preferred embodiment and best mode of the invention is shown by FIGS. 3 and 4. Representative prior art is shown by FIGS. 1 and 2. In FIGS. 3 and 4 the inventive chemotaxis chamber assembly 10 is a four-tiered instrument made of clear acrylic with two smooth surfaced middle plates 12 and 14 provided with respective threaded throughgoing apertures 13 and 15 and two additional clear acrylic plates forming the top plate 16 and bottom plate 18. It should be noted that any suitable material could be used as the material of the plates but the same are preferably of a clear and an inert material.

One unique feature of the present invention is the use of a double set of stainless steel hardware comprising a suitable number of bolts which would provide effective sealing between the plates, filter and gaskets. One set of six stainless steel bolts 20 having a head 21 with a threaded portion 23 adjacent to the head and a threaded portion 23a remote from the threaded portion 23 distal from head 21 enters the assembly through throughgoing holes in the bottom plate 18 and with the gasket 22 threadably seals the bottom plate 18 to the lower middle plate 14 via the engagement of threaded portion 23 into threaded aperture 15. A second set of stainless steel bolts 24 having a head 21 with a threaded portion 25 adjacent to the head and a threaded portion 25a remote from the threaded portion 25 and distal from head 21 enters surface 17 and the associated bolt seat 27 of the top plate 16 into throughgoing holes in the top plate 16 and likewise pinches a gasket 26 between the top plate 16 and the threadably attached upper middle plate 12. The threaded portion 25 of bolt 24 is threaded in the threaded aperture 13 of the upper middle plate 12, holding plate 16, gasket 26 and upper middle 12 in a fixed secured relationship. The bottom plate 18, lower middle plate 14 and associated gaskets are removably held in place by thumb nuts or standard nuts 32 fixedly attached to distal threaded portion 25a. It is of course apparent that compartment assemblies work in the same manner.

While the present embodiment uses threaded bolts, any other suitable types of securing means known in the prior art which accomplish the same sealing results and sectionality of a compartment could be used. With the hardware thus installed, the bottom/lower middle plate group 18, 14 and top/upper middle plate group 16, 12 form two assay sections with closed or blind wells 28 numbering 48 separate wells. Each set of six hardware bolts 20, 24 is not positioned in the same hole pattern. Therefore, in the top/upper middle plate group 16, 12 bolts 24 are screwed in threaded aperture 13 of plate 12 and penetrate an unoccupied set of holes in the bottom/middle plate group 18/14 and vice versa. The upper and lower plate groups are joined with an interposed gasket and filter 30 of polycarbonate or cellulose nitrate to form 48 sealed chambers or blind wells 28 of 50 μl each. It is apparent that the chambers or wells could vary in number from the number set forth; either being greater or lesser as desired. The filter is preferably 25×80 mm and constructed of a polycarbonate membrane having a pore size ranging from 1 to 8 microns diameter. The filter can also be coated with TYPE 1 collagen, TYPE IV collagen, fibronectin or laminin if desired. It is also envisoned that the filters could be constructed of any suitable porous material.

The chambers are designed so that the thumb nuts 32 mounted in recesses 34 on surfaces 17 and 19 tie the two plate sets together and do not bear on both the top and bottom plates 16 and 18. This allows each set of six bolts with associated thumb nuts installed to join the middle late either to the bottom or top pair. Consequently either the top or bottom plate can be removed without disturbing the seal between the two middle plates 12, 14 and the filter 30. This permits free access to the upper wells (cell compartment) 40 and lower wells (pseudopodia compartment) 50 without disturbing the cell plate at any time during the assay. With a filter and gasket 22 and 26 interposed between the top and bottom sections, the fully assembled instrument creates 48 closed wells separated by a filter.

It is further envisioned that the plates could be sectioned so that only a portion of the cells on a particular side are exposed.

An experiment is started by filling the 48 wells in the assembled bottom section 50. A filter 30 can then be placed over the filled wells and the upper middle plate 12, attached with thumb nuts. The assay instrument can then be incubated without the top plate 16 attached. After incubation the top plate 16 is attached, the chamber inverted and the bottom plate 18 removed without breaking the seal of the filter 30 between the middle plates 12 and 14. This allows access to the bottom wells on the bottom side of the filter where cells or cell pseudopods may be studied or fluid sampled or replaced. Thus it can be seen that the hardware is designed so that either the top plate or the bottom plate can be removed without disturbing the seal between the three other plates.

While the general embodiments of the present invention have been described, it will be apparent to those of ordinary skill in the art that various alternative configurations and embodiments can readily be adapted to the present invention and are considered to fall within the scope thereof as set forth in the following claims.

What we claim is:

1. A chemotaxis assay instrument comprising a bottom plate, seal means mounted to said bottom plate, an intermediate plate mounted on the other side of said seal means and spaced by said seal means from said bottom plate, said intermediate plate defining a plurality of wells to hold a sample, a filter mounted to said intermediate plate, a second intermediate plate spaced from said first intermediate plate by said filter, second seal means mounted to said second intermediate plate, a top plate mounted to said second seal means spaced by said second seal means from said second intermediate plate, and means to hold said plates together in a sealed relationship.

2. An instrument as claimed in claim 1 wherein said holding means comprises a plurality of bolts.

3. An instrument as claimed in claim 2 wherein said bolts are positioned on said top plate and said bottom plate end are offset from each other.

4. An instrument as claimed in claim 1 wherein said top, bottom, and intermediate plates are constructed of clear acrylic plastic.

5. An instrument as claimed in claim 2 wherein said bolts are constructed of stainless steel.

6. An instrument as claimed in claim 1 wherein said seal means are polycarbonate membranes.

7. An instrument as claimed in claim 1 wherein said filter is constructed of polycarbonate.

8. An instrument as claimed in claim 1 wherein said plates are attached together with thumbnuts.

9. An instrument as claimed in claim 1 wherein said assembled instrument creates two separated compartments, each of which has a plurality of closed wells separated by a filter.

10. An instrument as claimed in claim 9 wherein said closed wells are at least 48 in number.

11. An instrument as claimed in claim 1 wherein said instrument forms a plurality of wells having a cell compartment and a pseudopodia compartment.

12. An instrument as claimed in claim 1 wherein said intermediate plates define a plurality of wells.

13. An instrument as claimed in claim 1 wherein said filter is a polycarbonate membrane with a pore size ranging from 1 to 8 microns.

14. An instrument as claimed in claim 1 wherein said filter is constructed of polycarbonate coated with TYPE I collagen.

15. An instrument as claimed in claim 1 wherein said filter is constructed of polycarbonate coated with TYPE II collagen.

16. An instrument as claimed in claim 1 wherein said filter is constructed of polycarbonate coated with fibronectin.

17. An instrument as claimed in claim 1 wherein said filter is constructed of polycarbonate coated with laminin.

18. A cell culture apparatus for cell assay comprising a plurality of cell-impermeable plates, at least two plates defining a plurality of cell culture wells separated by a filter membrane of porous construction having a pore size suitable to allow the pseudopods of cells to pass therethrough without allowing the nucleus of the cell to pass therethrough, outer plates spaced from the outer surface of each of said two plates by a filter member between each outer plate and the adjacent inner plate and locking means holding said plates in a fixed sealed relationship.

19. A cell culture apparatus as claimed in claim 18 wherein said locking means comprises a plurality of fasteners mounted to one outer plate and at least its adjacent spaced plate and a second plurality of fasteners mounted to the other outer plate and at least its adjacent spaced plate positioned offset from said first plurality of fasteners.

20. A cell culture apparatus as claimed in claim 18 wherein said filter membrane has throughgoing pores ranging from 1-8 microns in size.

21. A cell culture apparatus as claimed in claim 18 wherein said plates are constructed of a clear plastic.

22. A selective access dual compartment cell culture assay device comprising two plates defining a plurality of cell culture wells separated by a membrane having a pore size ranging from 2-8 microns, at least one sheet of gas permeable, liquid impermeable material mounted to the opposite side of each of said plates, an end plate mounted opposite each plate and spaced from said plate by said sheet of gas permeable, liquid impermeable material and locking means securing at least said one plate and its respective opposing end plate together to form a first compartment and said other plate and its respective opposing end plate together to form a second compartment and means to hold all of said plates together in a fixed sealed relationship.

* * * * *